(12) United States Patent
Epstein et al.

(10) Patent No.: US 8,415,364 B2
(45) Date of Patent: Apr. 9, 2013

(54) METHOD OF PREVENTING OR TREATING GLAUCOMA

(75) Inventors: David L. Epstein, Bahama, NC (US); Paul P. Lee, Capel Hill, NC (US); Vasanth Rao, Cary, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 10/580,477

(22) PCT Filed: Nov. 26, 2004

(86) PCT No.: PCT/US2004/039657
§ 371 (c)(1),
(2), (4) Date: Jan. 25, 2007

(87) PCT Pub. No.: WO2005/053683
PCT Pub. Date: Jun. 16, 2005

(65) Prior Publication Data
US 2007/0161699 A1    Jul. 12, 2007

Related U.S. Application Data

(60) Provisional application No. 60/524,912, filed on Nov. 26, 2003.

(51) Int. Cl.
*A61K 31/41* (2006.01)
*A61K 31/55* (2006.01)
*A61K 31/505* (2006.01)

(52) U.S. Cl.
USPC .................. 514/275; 514/277; 514/359

(58) Field of Classification Search ............... 514/275, 514/277, 359, 913
See application file for complete search history.

(56) References Cited

U.S. PATENT DOCUMENTS

| | | | |
|---|---|---|---|
| 3,983,140 A | 9/1976 | Endo et al. | |
| 4,231,938 A | 11/1980 | Monaghan et al. | |
| 4,346,227 A | 8/1982 | Terahara et al. | |
| 4,444,784 A | 4/1984 | Hoffman et al. | |
| 4,450,171 A | 5/1984 | Hoffman et al. | |
| 4,681,893 A | 7/1987 | Roth | |
| 4,739,073 A | 4/1988 | Kathawala | |
| 5,041,450 A | 8/1991 | Chiou et al. | |
| 5,134,124 A * | 7/1992 | Nisato et al. .......... | 514/19 |
| 5,177,080 A | 1/1993 | Angerbauer et al. | |
| 5,273,995 A | 12/1993 | Roth | |
| 5,284,953 A | 2/1994 | Ohara et al. | |
| 5,354,772 A | 10/1994 | Kathawala | |
| 5,356,896 A | 10/1994 | Kabadi et al. | |
| 5,536,814 A | 7/1996 | Ruoslahti et al. | |
| 5,629,294 A | 5/1997 | diZerega et al. | |
| 5,683,867 A | 11/1997 | Biesecker et al. | |
| 5,733,558 A | 3/1998 | Breton et al. | |
| 5,753,230 A | 5/1998 | Brooks et al. | |
| 5,811,515 A | 9/1998 | Grubbs et al. | |
| 5,856,336 A | 1/1999 | Fujikawa et al. | |
| 5,900,414 A | 5/1999 | Sugrue et al. | |
| 2003/0207925 A1 | 11/2003 | Cameron et al. | |
| 2004/0248972 A1 * | 12/2004 | Lockhart et al. ............ | 514/460 |
| 2005/0239871 A1 | 10/2005 | Hellberg et al. | |

FOREIGN PATENT DOCUMENTS

| | | |
|---|---|---|
| CA | 2018209 | 12/1990 |
| EP | 363934 | 4/1990 |
| EP | 491226 | 6/1992 |
| EP | 738510 | 10/1996 |
| EP | 1298223 | 4/2003 |
| JP | 03-034934 | 2/1991 |
| JP | 07-188284 | 7/1995 |
| JP | 10-17488 | 1/1998 |
| JP | 2000-336042 | 12/2000 |
| JP | 2003-180399 | 7/2003 |
| JP | 2003-292442 | 10/2003 |
| JP | 2004149480 | 5/2004 |
| WO | WO 97/06791 | 2/1997 |
| WO | 00/09162 | 2/2000 |
| WO | 01/54728 | 8/2001 |
| WO | 01/97751 | 12/2001 |
| WO | 02/067901 | 9/2002 |
| WO | 03/051822 | 6/2003 |
| WO | 03/077910 | 9/2003 |
| WO | 03/080070 | 10/2003 |
| WO | 03/086380 | 10/2003 |
| WO | WO 2005/105155 | 11/2005 |

OTHER PUBLICATIONS

Chavis, P.S. et al., "Risk factors for age-related macular degeneration," Invest. Opthalmol. (2003) 44(5), Abstract.
Japanese Patent Office Action for Application No. 2006-541438 dated Oct. 21, 2010 (9 pages) with English translation.
Endo, A. et al., "Dihydromonacolin L and Monacolin X, new metabolites which inhibit cholesterol biosynthesis," J. Antibiotics (1985) XXXVIII (3):321-327.
International Search Report and Written Opinion for Application No. PCT/US04/39657 dated Apr. 25, 2005 (4 pages).
European Search Report for Application No. 04812221.2 dated Nov. 19, 2008 (4 pages).
European Office Action for Application No. 04812221.2 dated Aug. 27, 2009 (4 pages).
European Patent Office Action for Application No. 04812221.2 dated Sep. 27, 2011 (4 pages).
Amemiya, T. et al., "Relationship between data from complete medical checkup and change in ocular fundus with glaucoma," Magazine for Yamanashi Medical College (1999) 14(10):1465-1468, with partial translation.
Eto, M. et al., "Statin prevents tissue factor expression in human endothelial cells: role of Rho/Rho-kinase and Akt pathways," Circulation (2002) 105(15):1765-1769.
Fukunaga, A., "Cases of geriatric disease and clinical practice, study for the effect of pravastatin administration to function of vascular endothelium," Geriatric Medicine (2003) 41(10):1509-1512, with partial translation.

(Continued)

*Primary Examiner* — Zohreh Fay
(74) *Attorney, Agent, or Firm* — Michael Best & Friedrich LLP

(57) ABSTRACT

The present invention relates, in general, to glaucoma and, in particular, to a method of preventing or treating glaucoma using statins.

20 Claims, 1 Drawing Sheet

OTHER PUBLICATIONS

Ichiki, T., "Angiotensin II and Rho/Rho-kinase," Japan Clinical (2002) 60(10):1929-1933, with partial translation.

Noda, Y. et al., "Vasodilatory action of angiotension II receptor antagonist (CS-088) in bovine retinal blood vessel using microvessel perfusion system," New Ophthalmology (2003) 20(10):1465-1468, with English translation.

Tokushige, H., "ROCK inhibitor and glaucoma," Bioclinica (2002) 17(13):61-64, with English translation.

Yokoyama, K. et al., "HMG-CoA reductase inhibitors suppress intracellular calcium mobilization and membrane current induced by lysophosphatidylcholine in endothelial cells," Circulation (2002) 105(8):962-967.

Japanese Patent Office Action for Application No. 2006-541438 dated May 25, 2011 (10 pages) with English translation.

Collaborative Normal-Tension Glaucoma Study Group, "Comparison of Glaucomatous Progression Between Untreated Patients with Normal-Tension Glaucoma and Patients with Therapeutically Reduced Intraocular Pressures," *American Journal of Ophthalmology*, vol. 126, No. 4. Oct. 1998, pp. 487-497, Elsevier Science Inc., 1998.

Avila, Marcel, et al., "The Effects of RGD (Arg-Gly-Asp) Peptides on Glaucoma Filtration Surgery in Rabbits," *Ophthalmic Surgery and Lasers*, Apr. 1998, vol. 29, No. 4, pp. 309-317.

Comparato, C., et al., "Clinically relevant pleiotropic effects of statins: Drug properties or effects of profound cholesterol reduction?" *Nutrition, Metabolism and Cardiovascular Diseases*, vol. 11, No. 5, Oct. 2001, pp. 328-343, Medikal Press s.r.l., Milan, Italy.

Edwards, Peter A., and Johan Ericsson, "Sterols and Isoprenoids: Signaling Molecules Derived from the Cholesterol Biosynthetic Pathway," *Annual Review of Biochemistry*, vol. 68, 1999, pp. 157-185, Annual Reviews, Palo Alto, California.

Hall, Nigel F., et al., "Risk of macular degeneration in users of statins: cross sectional study," *BMJ*, 2001, 323 (7309), pp. 375-376, http://bmj.bmjjournals.com/cgi/content/full/323/7309/375.

Hershkoviz, Rami, et al., "Nonpeptidic Analogues of the Arg-Gly-Asp (RGD) Sequence Specifically Inhibit the Adhesion of Human Tenon's Capsule Fibroblasts to Fibronectin," *Investigative Ophthalmology & Visual Science*, Apr. 1994, vol. 35, No. 5, pp. 2585-2591, Association for Research in Vision and Ophthalmology.

Kagansky, N., et al., "Cholesterol lowering in the older population: time for reassessment?," *QJM*, vol. 94, No. 9, Sep. 2001, pp. 457-463, Oxford University Press, Association of Physicians, 2001.

Kass, Michael A., "The Ocular Hypertension Treatment Study," *Archives of Ophthalmology*, vol. 120, Jun. 2002, pp. 701-713, American Medical Association.

Laties, Alan M., et al., "Expanded Clinical Evaluation of Lovastatin (EXCEL) Study Results II. Assessment of the Human Lens After 48 Weeks of Treatment with Lovastatin," *The American Journal of Cardiology*, Mar. 1, 1991. vol. 67, No. 6, pp. 447-453.

Lowenstein, John M., ed., *Methods in Enzymology*, "Lipids," Part C, vol. 71, pp. 455-509, Academic Press, Inc., New York, 1981.

McCarty, Catherine A., et al., "Cholesterol-lowering medications reduce the risk of age-related maculopathy progression," *The Medical Journal of Australia*, vol. 175, No. 6, Sep. 17, 2001, p. 340, Australian Medical Association.

McGwin, Gerald, Jr., et al., "Statins and Other Cholesterol-Lowering Medications and the Presence of Glaucoma," *Arch Ophthalmol*, vol. 122, Jun. 2004, pp. 822-826.

McGwin, Gerald, Jr., et al., "The association between statin use and age related maculopathy," *British Journal of Ophthalmology*, 2003; 87, pp. 1121-1125, from www.bjophthalmol.com, Jul. 6, 2006.

Pardridge, William M., *Peptide Drug Delivery to the Brain*, p. 247, Raven Press, New York, 1991.

Rao, P. Vasantha, et al., "Modulation of Aqueous Humor Outflow Facility by the Rho Kinase-Specific Inhibitor Y-27632," *Investigative Ophthalmology & Visual Science*, vol. 42, No. 5, Apr. 2001, pp. 1029-1037, Association for Research in Vision and Ophthalmology.

Ruoslahti, Erkki, and Michael D. Pierschbacher, "Arg-Gly-Asp: A Versatile Cell Recognition Signal," *Cell*, vol. 44, 517-18, Feb. 28, 1986, Cell Press, 1986.

Schlienger, Raymond G., et al., "Risk of Cataract in Patients Treated with Statins," *Archives of Internal Medicine*, vol. 161, Sep. 10, 2001, pp. 2021-2026, American Medical Association, Chicago, IL.

Shovman, Ora, et al., "Antiinflammatory and Immunomodulatory Properties of Statins," *Immunologic Research*, 25/3, pp. 271-285, Humana Press Inc., 2002.

Song, Julia, et al., "Effects of Cholesterol-Lowering Statins on the Aqueous Humor Outflow Pathway," *Investigative Ophthalmology & Visual Science*, Jul. 2005, vol. 46, No. 7, pp. 2424-2432, Association for Research in Vision and Ophthalmology.

Song, Julia, et al., "Effects of cholesterol lowering statin drugs on the aqueous humor outflow pathways," webpage: http://www.abstractsonline.com/viewer/viewAbstractPrintFriendly.asp?CKev={56E3C070- . . . Apr. 6, 2004, Oasis, Online Abstract Submission and Invitation System—Program Planner, one page abstract.

Takemoto, Masao, and James K. Liao, "Pleiotropic Effects of 3-Hydroxy-3-Methylglutaryl Coenzyme A Reductase Inhibitors," *Journal of the American Heart Association*, vol. 21, No. 11, Nov. 2001, pp. 1712-1719, American Heart Association, Inc., 2001.

Yalpani, Manssur, "Cholesterol-lowering drugs," *Chemistry & Industry*, No. 3, Feb. 5, 1996, pp. 85-89, Society of Chemical Industry, East Sussex, UK.

\* cited by examiner

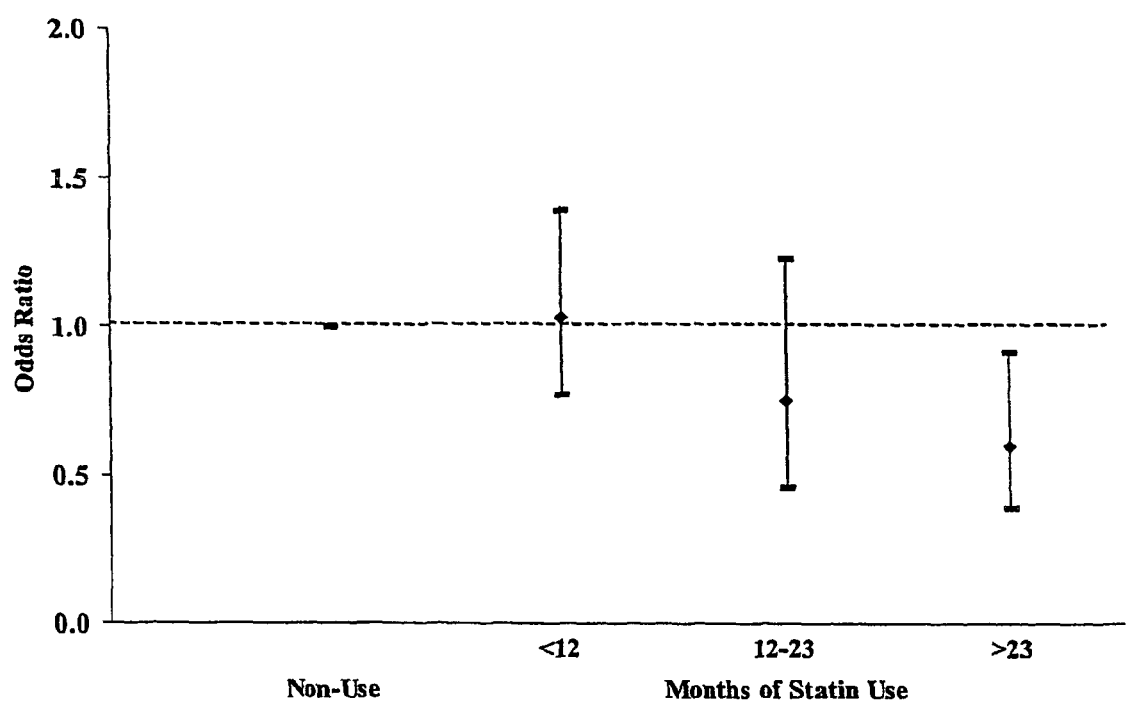

METHOD OF PREVENTING OR TREATING GLAUCOMA

This application claims priority from U.S. Provisional Application No. 60/524,912, filed Nov. 26, 2003, the entire content of which is incor herein by reference.

TECHNICAL FIELD

The present invention relates, in general, to glaucoma and, in particular, to a method of preventing or treating glaucoma using statins.

BACKGROUND

Glaucoma is one of the three leading causes of blindness in the United States and it is a leading cause of blindness in the world. Over 2.2 million people in the United States have glaucoma, and several million more are at risk of developing the disease. As the population ages, the number of individuals with glaucoma will continue to grow since glaucoma affects the oldest individuals disproportionately.

Glaucoma is not just one disease, rather, it is a spectrum of conditions that share a final common pathway of acquired, progressive deterioration of the neuronal components of the optic nerve. Neuronal death results in loss of vision once a sufficient number of individual nerves are destroyed.

Factors associated with the development of glaucoma and its progression have been identified and are in the process of being clarified. Elevated intraocular pressure (IOP) is the leading cause of glaucoma. Pressure is elevated because drainage of aqueous fluid from within the eye is impaired. Current treatments for glaucoma center on reducing pressure in the eye by reducing the amount of aqueous fluid being produced or by enhancing the flow of fluid out of the eye by mechanical or other means. Currently available drugs do not enhance or restore functioning of the natural drainage pathway.

Glaucoma patients may also suffer reduced blood flow to the optic nerve and neuronal tissue, diminished resistance of the nerve tissue to damage, and compliance of connective tissue surrounding and supporting the optic nerve. Current treatments do not address any such factors. Only one agent, Memantine, is in phase III clinical trials (Allergan) as an agent that may increase the relative resistance of the nerve tissue to damage (i.e., neuroprotective).

The use of statins has been associated in some studies with a diminished risk of developing age-related macular degeneration as well as a potential for reducing the risk for several medical conditions related to cardiovascular disease (Hall et al, BMJ 323:375-376 (2001), McCarty et al, MJA 175:340 (2001), Shovman et al, Immunol. Res. 25:271-285 (2002), Kagansky et al, QJM 94:457-463 (2001)). The presumed direct causal mechanisms have centered on the effect of 3-hydroxy-3-methylglutaryl coenzyme A (HMG-CoA) reductase inhibitors in reducing cholesterol production and enhancing LDL-cholesterol removal from plasma. To the extent that excess total cholesterol or LDL cholesterol is implicated in these conditions, use of the statins would reduce the risk of developing, or at least delay the onset of, these conditions. Statins also inhibit non-steroidal isoprenoid production (Edwards and Ericsson, Annu. Rev. Biochem. 68:157-185 (1999), Comparato et al, Nutr. Metab. Cardiovasc. Dis. 11:328-343 (2001), Takemoto and Liao, Arterioscler. Throm. Vasc. Biol. 21:1712-1719 (2001)). Many statins also inhibit the activity of rho-kinase, such inhibition has been shown to enhance aqueous outflow (Rao et al, Invest. Ophthalmol. & Vis. Sci. 42:1029-1037 (2001)). There may, of course, be as yet undiscovered or indirect effects of these compounds that would help explain their protective associations.

The present invention provides a new approach to the field of therapeutics for patients with glaucoma. Provided is a method of preventing or treating glaucoma using statins.

SUMMARY OF THE INVENTION

The present invention relates generally to glaucoma. More specifically, the invention relates to a method of preventing glaucoma or reducing the risk of glaucoma development using statins. The invention also relates to a method of treating glaucoma using statins.

Objects and advantages of the present invention will be clear from the description that follows.

BRIEF DESCRIPTION OF THE DRAWINGS

FIG. 1. Significant trend towards a reduced risk of glaucoma with longer statin use.

DETAILED DESCRIPTION OF THE INVENTION

The present invention relates to the use of statins to reduce the risk of glaucoma development in a patient. The invention further relates to a method of treating glaucoma or inhibiting progression of the disease.

The term statin refers to compounds that inhibit the transformation of hydroxymethylglutarylcoenzyme A (HMG-CoA) to mevalonic acid as catalyzed by the enzyme HMG-CoA reductase. Compounds capable of effecting such inhibition can be identified readily by one skilled in the art using standard assays (see, for example, Methods of Enzymology 71:455-509 (1981) and references cited therein).

Examples of statins suitable for use in the present invention include the natural fermentation products, mevastatin and lovastatin, as well as semi-synthetic and totally synthetic statins described, for example, in U.S. Pat. Nos. 3,983,140, 4,231,938, 4,346,227, 4,444,784, 4,450,171, 4,681,893, 4,739,073, 5,177,080, 5,273,995, 5,284,953, 5,354,772, 5,356,896, and 5,856,336, and in European Patent Application Nos. 738,510 A2 and 363,934 A1 and EP 491,226. Additional examples of HMG-CoA reductase inhibitors suitable for use in the invention are described in Yalpani, "Cholesterol Lowering Drugs", Chemistry & Industry, pp. 85-89 (1996).

Preferably, the statin used in the present method is mevastatin, lovastatin, pravastatin, velostatin, simvastatin, fluvastatin, cerivastatin (rivastatin), dalvastatin, fluindostatin or atorvastatin, or a prodrug thereof, or a pharmaceutically acceptable salt of such statin or prodrug. More preferably, the statin is lovastatin (MEVACOR (U.S. Pat. No. 4,231,938)), sinvastatin (ZOCOR (see U.S. Pat. No. 4,444,784)), pravastatin (PRAVACHOL (see U.S. Pat. No. 4,346,227)), fluvastatin (LESCOL (U.S. Pat. No. 5,354,772)), atorvastatin (LIPITOR (U.S. Pat. No. 5,273,995)), cerivastatin (U.S. Pat. No. 5,177,080)) or nivastatin (NK-104 (U.S. Pat. Nos. 5,284, 953, 5,356,896 and 5,856,336)).

Methods of producing suitable statins are described, for example, in one or more of the above cited patents/patent applications.

Statins suitable for use in the invention can be formulated into pharmaceutical compositions, for example, as described in the above-referenced patents/applications. The statin is preferably formulated in a form suitable for oral administration, for example, as a tablet or capsule. Optimum dosing regimens can be established by one skilled in the art without undue experimentation. While dosing regimens used for glaucoma treatment/prevention can be the same as regimens used for lowering cholesterol, optimum regimens can be readily established by one skilled in the art.

Combination therapy can also be used in the methods of the present invention. That is, a selected statin can be used in combination with another medicament(s) known to be useful for the treatment of glaucoma. Examples of agents that can be used in combination with statins in the present invention include β-adrenergic blocking agents, carbonic anhydrase inhibitors, miotics, sympathomimetics and prostaglandin agonists. Specific examples of currently available medicaments suitable for use in combination with statins include Latanoprost (Xalatan), Bimatoprost (Lumigan), Travoprost (Travatan), and Unoprostone (Rescula). A selective $EP_4$ receptor agonist or prodrug thereof as described in U.S. Patent Application 20030207925 may or may not be used in combination with statins in the present methods. Most medicaments presently used for glaucoma treatment are administered as droplets to the eye. Statins can also be administered as droplets to the eye but have the advantage of being administerable orally as well. Therefore, when combination therapy is used, the dosage forms can be the same or they can differ (e.g., the statin may be present in a form suitable for oral administration while the other medicament may be present as eye droplets (or they can both be administered as droplets to the eye)). The compounds can be administered at essentially the same time or at different times.

It will be appreciated from the present disclosure that the present methods have application in the human therapeutic strategies and in veterinary settings as well.

With a greater understanding of the multiple mechanisms that could potentially impact the outflow system or the optic nerve in glaucoma, there are plausible means by which statin use could be associated with a reduced risk of developing glaucoma. While not wishing to be bound by theory, it is noted that by reducing atherosclerotic processes and subsequent vascular diseases, statins may directly protect optic nerve head vasculature or may indirectly improve ocular blood flow. Since the trabecular meshwork has endothelial cells that share many attributes of vascular endothelial cells, statins may also exert a protective effect in enhancing trabecular endothelial cell function. Additionally, many statins also inhibit the activity of rho-kinase, such inhibition has been shown to result in an increase in aqueous outflow.

Certain aspects of the invention can be described in greater detail in the non-limiting Examples that follows.

Example 1

Experimental Details

Study Population and Data Source

The Birmingham (Ala.) Department of Veterans Affairs Medical Center (BVAMC) is 134-bed acute tertiary care medical facility and serves as a Veterans Hospital Administration tertiary care referral center for Alabama. All patients who had at least one visit (inpatient or outpatient) at the Birmingham BVAMC between a specified period were eligible for study inclusion. Because the prevalence of glaucoma is low below age 50, the study population was limited to patients 50 and older. Females were also excluded as they represented such a small proportion of the patient population (10.8%) that meaningful analyses were impossible.

The BVAMC provided data files containing demographic information (age, gender, race) and clinical and medication information for each patient. The clinical file contained a description of each diagnosis made at the BVAMC during inpatient and outpatient visits and the diagnosis date. All diagnoses were coded using the International Classification of Diseases, Ninth Revision, Clinical Modification (ICD-9CM). The medication file contained information on each medication prescribed during each patient visit. This file also contained the prescription date and the date the prescription was filled. For both the clinical and medication files, the information provided pertained to all diagnoses and medications over the course of each patient's history with the BVAMC and not just those that occurred in the specified time period.

Study Design

Within the study population, a nested case-control study was conducted. Cases of glaucoma were defined using the ICD-9CM codes 365.1 (open-angle glaucoma), 365.8 (other specified forms of glaucoma) and 365.9 (unspecified glaucoma). It was believed that the use of the non-specified forms of glaucoma were likely to reflect open-angle glaucoma that was imprecisely coded. To the extent that they truly represent other forms of glaucoma that are not associated with statin use, the bias so introduced would be towards the null.

Information on the glaucoma diagnosis date was procured and is referred to below as the index date. Because this study addressed the association between statin use and the new diagnosis of glaucoma, patients who had a glaucoma diagnosis prior to the observation period of the study (prevalent cases) were excluded.

Controls were randomly selected from the study population who did not have a glaucoma diagnosis by the end of the observation period. To be considered an eligible control for a given case, the control must have had an encounter with the BVAMC (inpatient or outpatient) on or before the index date of the matched case. Ten controls were selected for each case and matched on age (±1-year). Each control was assigned the index date associated with their matched case.

The prescription file was queried for the presence of filled statin (atorvastatin, cerivastatin, fluvastatin, pravastatin, simvastatin, lovastatin) prescriptions. Non-statin lipid-lowering agents (e.g., fibrates, nicotinic acid) were also extracted from the prescription file. Only those prescriptions that were filled prior to the index date for each matched set of cases and controls were considered. Time since first statin use was calculated as the time between the first statin prescription and the index date. Statin users, were also classified as being current or past users with the former being those who had a statin prescription filled within 6 months before the index date and the latter being those whose last prescription fill date was greater than 6 months before the index date. An analogous set of variables was created for the non-statin lipid-lowering agents.

Information on the presence of the following conditions was extracted from the clinical data file: ischemic heart disease (ICD-9CM codes 410 though 414), cerebrovascular disease (ICD-9CM codes 430 though 438), lipid metabolism disorders (ICD-9CM code 272), hypertension (ICD-9CM codes 401 though 405), diseases of the arteries, arterioles and capillaries (ICD-9CM codes 440 though 448), and diabetes (ICD-9CM code 250). For the purposes of analysis, only those diagnoses that were recorded prior to the index date were considered.

Statistical Analysis

Conditional logistic regression was used to calculate an odds ratio (OR) and 95% confidence interval (CI) for the association between any statin use and the risk of developing glaucoma. ORs and 95% CIs were also estimated for current and past statin users relative to non-users and according to time since first prescription. A similar set of analyses was conducted for non-statin lipid-lowering agents. Stratified analyses were conducted to determine if diabetes, lipid metabolism disorders, hypertension, cardiovascular disease, cerebrovascular disease, and arterial disease modified the association between statin use and glaucoma. There were an insufficient number of patients using non-statin lipid-lowering agents to conduct a similar set of stratified analyses.

Results

Table 1 presents the demographic and medical characteristics among the glaucoma cases and control. By design, the mean age of both cases and controls was equivalent. There were twice as many African-Americans among the cases compared to controls. Those with glaucoma were more likely to also have diabetes, lipid metabolism disorders, and hypertension.

Table 2 demonstrates the statin and non-statin medication use characteristics among glaucoma cases and non-glaucoma controls, as well as the unadjusted and adjusted ORs. While cases were more likely to have filled a statin prescription (OR 1.23, 95% CI 0.99 to 1.51), following adjustment for diabetes, lipid metabolism disorders, hypertension, cardiovascular disease, cerebrovascular disease, and arterial disease, a protective association was observed (OR 0.85, 95% CI 0.66 to 1.09), albeit not statistically significant. This association was observed, albeit not significantly, for past (OR 0.74, 95% CI 0.53 to 1.04) but not current (OR 0.94, 95% CI 0.70 to 1.27) statin use. There was a significant trend towards a reduced risk of glaucoma with longer term statin use (p=0.04) (FIG. 1). Indeed, use of statins for greater than 23 months was associated with a statistically significant reduction in the risk of glaucoma (OR 0.60, 95% CI 0.39 to 0.92).

Use of non-statin lipid lowering medications was also associated with a significantly reduced risk of glaucoma (OR 0.59, 95% CI 0.37 to 0.97) that was also apparent among both current and past users although neither association was statistically significant. However, this association was limited to those with <12 months of use (OR 0.38, 95% CI 0.18 to 0.79). When considering the joint effect of statin and non-statin medications, the largest risk reduction was associated with use of both types of medications (OR 0.52) followed by non-statin use only (OR 0.60) and statin use only (OR 0.86). However, none of these associations was statistically significant.

Table 3 presents ORs and 95% CIs for the association between statin use and glaucoma stratified according to the presence of combordities. Once the other medical characteristics are controlled for, significant associations between statin use and glaucoma were observed among those with lipid metabolism disorders, cardiovascular disease, and those without cerebrovascular disease.

Conclusions

The results of this analysis demonstrate a significant and meaningful trend towards reduced risk of glaucoma development with longer-term statin use, particularly two or more years. Evaluating larger datasets with longer follow-up periods, such as those with managed care companies or with insurance company claims files where both disease and pharmacy data are maintained, would allow a more definitive evaluation of the usefulness of statins as an additional therapy for glaucoma or its prevention.

Such an endeavor is clearly worthwhile, based not only on the results of the current study but also on some plausible potential mechanisms whereby such a protective effect might occur. First, many statins inhibit the activity of rho-kinase; such inhibition has been shown to enhance aqueous outflow, thereby presumably lowering IOP (Rao et al, Invest. Ophthalmol. & Vis. Sci. 42:1029-1037 (2001)). It would be interesting to examine the effect of statin use on the level of IOP, controlling for the status of glaucoma and the intensity of treatment. Second, the ability of statins to reduce cardiovascular disease may directly or indirectly protect the vascular supply to the optic nerve or eye. Interestingly, statin use is associated with a higher, albeit not statistically meaningful, elevation of risk of glaucoma among those with cerebrovascular disease compared to a lower risk among those with cardiovascular diasease. This may indicate that the direct and indirect mechanisms have opposing effects or that there are additional factors at work.

If the trend and the magnitude of the effect seen with statin use of greater than 23 months is upheld with larger sample sizes in future studies, the protective effect is substantial and of similar magnitude to the benefit of lowering IOP through the use of medications in the OHTS study and of other treatments in other studies (Kass et al, Arch. Ophthalmol. 120: 701-713 (2002), Collaborative Normal Tension Study Group Am. J. Ophthalmol. 126:487-497 (1998)). This would also imply that a new therapeutic class of agents might be effective for the care and treatment of glaucoma patients.

The side effects of statins on ocular structures have been studied to a limited degree. While animal models might indicate a higher risk of cataract development due to the rho-kinsase inhibition of statins, human studies have demonstrated no elevated risk of cataracts among those taking statins (Schlienger et al, Arch. Intern. Med. 161:2021-2026 (2001), Laties et al, Am. J. Cardiology 67:447-453 (1991)). Obviously, longer-term follow-up over many years will be needed to be able to conclude that such chronic use is completely safe for the eye. In addition, the potential systemic side effects of statins need to be carefully considered.

The intriguing finding of some protective association with non-statin use also raises the possibility that lipid diseases as a whole may be associated with the presence of glaucoma, as seen in the higher proportion of cases with lipid disorders compared to controls. There have been no studies to suggest this is the case in population-based evaluations to date. Nevertheless, the associations found here, both in the protective association with cholesterol lowering agents and the higher rate of lipid disorders seen in those with glaucoma compared to controls, suggests that such inquiry is warranted. Thus, additional work is also needed to clarify the nature of the association between the presence of lipid disorders and the use of medications to lower lipid.

The evidence in favor of an independent role for treatment, however, is found in the significant OR of 0.63 among those with lipid disorders who have received statin treatment compared to those who have not, even after adjusting for co-morbid conditions.

Among those without cerebrovascular disease, statin use was protective for the development of glaucoma (OR of 0.76, with a CI of 0.58 to 0.99) while those with cerebrovascular disease demonstrated a positive association between statin use and glaucoma (OR of 2.01, with a CI of 0.99 to 4.10). This result is difficult to interpret. This could be a spurious association or an anomaly in the data or results. Alternatively, it may reflect the more general state of vascular supply to the central nervous system. Those without a history of cerebrovascular disease have a statin association similar to the other subpopulations and the population as a whole in this study. Those with a history may reflect a strong difficulty in vascular flow that overrides the effects of statins, since even those who do not use statins have an elevated, albeit not significant, risk of glaucoma (OR of 1.65). Further, those who have such conditions and who have been placed on statins may have cerebrovascular disease of greater severity than those that do not.

The above study has certain limitations. First, the study population consisted entirely of men, since it was an older VA population. Additional research on the association between statin use and glaucoma among women is necessary. Second, the diagnoses of glaucoma were made by individual physicians without the use of standardized criteria, which could introduce significant differences relative to other studies and study populations. However, there is no reason to expect the diagnosis of glaucoma to have been biased by the use of statins. Third, the diagnoses were subject to miscoding into ICD-9 codes; again, however, there is no reason to suspect that bias would result from this. Fourth, no clinical data was available, so no comment can be made on the severity of glaucoma. Fifth, statin use was defined on the basis of a filled prescription within the BVAMC pharmacy service. This suggests that a patient with a statin prescription record but no matching fill record would be classified as a non-statin user even though he did indeed use statins by filling the prescription outside the BVAMC system. Such misclassification, however, would only bias to the null. Additionally, since over 90% of statin prescriptions were filled at the BVAMC, this is unlikely to have produced a significant effect. Finally, race was unknown for a large proportion of our study population (both cases and controls). However, the race distribution among those with known data was similar to what would be expected given population-based studies and thus unlikely to introduce spurious results in the analyses. Information on additional potentially confounding characteristics (e.g., smoking) was similarly not available.

An important methodological issue is the possibility of "left-censoring" in that many patients with pre-existing glaucoma would have been captured in the first year or two of the study, since case identification was made on the basis of the first visit at which an open-angle or unspecified type of glaucoma was diagnosed. Thus, it was expected that many of the "new diagnosis" cases of glaucoma were actually prevalent cases that were first seen at the BVAMC and recorded into the database and captured by the selection algorithm as a "new diagnosis" case due to the enrollment time intervals. This issue, however, is unlikely to detract from the findings noted here because there is no a priori reason to believe that prevalent cases would differ from incident cases for statin or other anti-lipid agents use.

Example 2

Trabecular meshwork (TM) and ciliary muscle cells possess smooth muscle-like properties that have been hypothesized to be involved in the regulation of aqueous outflow facility. The purpose of the following study was to investigate the effects of cholesterol lowering statin drugs, which are known to influence the Rho pathway, on cell shape, contractile properties, cytoskeletal integrity in TM and ciliary muscle cells, and aqueous outflow through the TM.

Experimental Details

Porcine primary trabecular meshwork (PTM) and ciliary muscle cells (PCM) were cultured and treated with lovastatin or compactin at concentrations of 25 µM and 50 µM. Effects on actin stress fibers (phalloidin staining) and focal adhesion formation (vinculin) were evaluated by immunofluorescence staining. Urea/glycerol polyacrylamide gel electrophoresis and Western blot analysis were utilized to investigate the effects of statins on myosin light chain (MLC) phosphorylation. Changes in cell shape were recorded using the phase contrast microscope. A constant flow organ culture perfusion system was used to measure outflow facility in perfused porcine eye anterior segments.

Results

PTM cells treated with lovastatin and compactin demonstrated dramatic changes in cell shape, with cells becoming rounded and separated from each other. These morphological changes were found to be reversible upon drug withdrawal. Within 24 hours of drug administration, there was evidence of actin depolymerization and loss of focal adhesions. Supplementation of cell culture media containing lovastatin with geranylgeranyl pyrophosphate completely reversed the changes in cell shape and cytoskeletal organization. Lovastatin and compactin also induced marked reduction in MLC phosphorylation indicative of cellular relaxation. Similar changes in cell shape, cytoskeletal organization and MLC phosphorylation were observed in PCM cells treated with statins. In an ongoing study, perfusion of porcine eye anterior chambers with 100 µM lovastatin caused a 48% drop in intraocular pressure at 72 hours, as compared to a 22% reduction in IOP in control eyes.

CONCLUSIONS

These data demonstrate that statins (e.g., lovastatin and compactin) induce cellular relaxation in TM and ciliary muscle cells via effects on cell shape, actin cytoskeletal integrity and MLC phosphorylation. These effects of statins appear to involve the isoprenylation of small GTP-binding proteins such as Rho GTPase. Furthermore, these statins demonstrated the ability to decrease IOP in an organ culture perfusion model indicating their potential use in glaucoma therapy.

All documents and other information sources cited above are hereby incorporated in their entirety by reference.

TABLE 1

Demographic and Medical Characteristics Among Glaucoma Cases and Non-Glaucoma Controls

| | Cases (N = 667) | Controls (N = 6667) | p-value |
|---|---|---|---|
| Demographic Characteristics | | | |
| Age (in years), mean | 69.0 | 69.0 | .9259 |
| Race, n (%) | | | .7576 |
| Caucasian | 252 (37.8) | 3162 (47.4) | |
| African-American | 193 (28.9) | 939 (14.1) | |
| Other | 9 (1.4) | 26 (0.4) | |
| Unknown | 213 (31.9) | 2540 (38.1) | |
| Medical Characteristics | | | |
| Diabetes, n (%) | 172 (25.8) | 818 (12.3) | <.0001 |
| Lipid metabolism disorders, n (%) | 100 (15.0) | 545 (8.2) | <.0001 |
| Hypertension, n (%) | 341 (51.1) | 1811 (27.2) | <.0001 |
| Cardiovascular disease, n (%) | 130 (19.5) | 1312 (19.7) | .9069 |
| Cerebrovascular disease, n (%) | 50 (7.5) | 453 (6.8) | .4943 |
| Arterial disease, n (%) | 41 (6.2) | 368 (5.5) | .5010 |

TABLE 2

Statin and Non-Statin Medication Use Characteristics Among Glaucoma Cases and Non-Glaucoma Controls and Associated Odds Ratios (ORs) and 95% Confidence Intervals (CIs)

|  | Cases (N = 667) | Controls (N = 6667) | OR (95% CI) | OR (95% CI)* |
|---|---|---|---|---|
| Statin Use Characteristics | | | | |
| Statin use, n (%) | | | | |
| No | 548 (82.2) | 5663 (84.9) | 1.00 | 1.00 |
| Yes | 119 (17.8) | 1004 (15.1) | 1.23 (0.99-1.51) | 0.85 (0.66-1.09) |
| Non use | 548 (82.2) | 5663 (84.9) | 1.00 | 1.00 |
| Current use | 71 (10.6) | 535 (8.0) | 1.37 (1.06-1.78) | 0.94 (0.70-1.27) |
| Past use | 48 (7.2) | 469 (7.0) | 1.06 (0.78-1.44) | 0.74 (0.53-1.04) |
| Duration of use (in months), n (%) | | | | |
| Non use | 548 (82.2) | 5663 (84.9) | 1.00 | 1.00 |
| <12 | 68 (10.2) | 507 (7.6) | 1.39 (1.06-1.81) | 1.03 (0.77-1.39) |
| 12-23 | 21 (3.2) | 191 (2.9) | 1.14 (0.72-1.80) | 0.75 (0.46-1.23) |
| >23 | 30 (4.5) | 306 (4.6) | 1.01 (0.69-1.49) | 0.60 (0.39-0.92) |
| Non-Statin Cholesterol Lowering Medication Use Characteristics | | | | |
| Non-statin agent use, n (%) | | | | |
| No | 647 (97.0) | 6441 (96.6) | 1.00 | 1.00 |
| Yes | 20 (3.0) | 226 (3.4) | 0.88 (0.55-1.40) | 0.59 (0.37-0.97) |
| Non use | 647 (97.0) | 6441 (96.6) | 1.00 | 1.00 |
| Current use | 8 (1.2) | 91 (1.4) | 0.88 (0.42-1.81) | 0.60 (0.29-1.27) |
| Past use | 12 (1.8) | 135 (2.0) | 0.89 (0.49-1.61) | 0.59 (0.32-1.09) |
| Duration of use (in months), n (%) | | | | |
| Non use | 647 (97.0) | 6441 (96.6) | 1.00 | 1.00 |
| <12 | 8 (1.2) | 138 (2.1) | 0.58 (0.28-1.18) | 0.38 (0.18-0.79) |
| =12 | 12 (1.8) | 88 (1.3) | 1.36 (0.74-2.50) | 0.95 (0.50-1.79) |
| Statin and Non-statin Use Characteristics | | | | |
| Neither statin nor non-statin | 538 (80.7) | 5558 (83.4) | 1.00 | 1.00 |
| Statin use only | 109 (16.3) | 883 (13.2) | 1.28 (1.03-1.59) | 0.86 (0.66-1.11) |
| Non-statin use only | 10 (1.5) | 105 (1.6) | 0.98 (0.51-1.89) | 0.60 (0.30-1.18) |
| Statin and non-statin use | 10 (1.5) | 121 (1.8) | 0.85 (0.45-1.64) | 0.52 (0.26-1.04) |

*Adjusted for diabetes, lipid metabolism disorders, hypertension, cardiovascular disease, cerebrovascular disease, and arterial disease.

TABLE 3

Odds Ratios (ORs) and 95% Confidence Intervals (CIs) for the Association Between Statin Use and Glaucoma Stratified According to Presence of Medical Conditions

|  | OR (95% CI) | OR (95% CI)* |
|---|---|---|
| Diabetes | | |
| No | 1.12 (0.87-1.46) | 0.79 (0.58-1.07) |
| Yes | 0.97 (0.67-1.40) | 0.91 (0.63-1.50) |
| Lipid metabolism disorders | | |
| No | 1.11 (0.85-1.46) | 0.97 (0.73-1.30) |
| Yes | 0.57 (0.37-0.88) | 0.63 (0.41-0.99) |
| Hypertension | | |
| No | 1.40 (1.01-1.95) | 1.05 (0.72-1.53) |
| Yes | 0.71 (0.54-0.94) | 0.75 (0.54-1.03) |
| Cardiovascular disease | | |
| No | 1.59 (1.23-2.06) | 0.98 (0.73-1.33) |
| Yes | 0.81 (0.55-1.18) | 0.63 (0.42-0.97) |
| Cerebrovascular disease | | |
| No | 1.17 (0.94-1.47) | 0.76 (0.58-0.99) |
| Yes | 1.65 (0.89-3.06) | 2.01 (0.99-4.10) |
| Arterial disease | | |
| No | 1.26 (1.01-1.57) | 0.86 (0.66-1.11) |
| Yes | 0.87 (0.42-1.80) | 0.74 (0.32-1.72) |

*Adjusted for diabetes, lipid metabolism disorders, hypertension, cardiovascular disease, cerebrovascular disease, and arterial disease where appropriate.

What is claimed is:

1. A method of treating or inhibiting the progression of glaucoma comprising administering to a patient in need thereof a compound that inhibits the HMG-CoA reductase-catalyzed transformation of HMG-CoA to mevalonic acid, wherein said compound is administered in an amount sufficient to effect said treatment or inhibition, and wherein said compound is a statin.

2. The method according to claim 1 wherein said statin is selected from the group consisting of mevastatin, lovastatin, pravastatin, velostatin, simvastatin, fluvastatin, cerivastatin, dalvastatin, fluindostatin, nivastatin and atorvastatin.

3. The method according to claim 2 wherein said statin is selected from the group consisting of lovastatin, simvastatin, fluvastatin, atorvastatin, cerivastatin and nivastatin.

4. The method according to claim 1 wherein said compound is administered orally.

5. The method according to claim 1 wherein said compound is administered directly to the eyes of said patient.

6. The method according to claim 1 further comprising administering to said patient an agent selected from the group consisting of a β-adrenergic blocking agent, carbonic anhydrase inhibitor, miotic, sympathomimetic and prostaglandin agonist.

7. The method according to claim 1 further comprising administering to said patient a selective $EP_4$ receptor agonist.

8. A method for the treatment of glaucoma in a patient which comprises administering a pharmaceutically effective amount of a composition comprising at least one HMG-CoA reductase inhibitor to said patient, wherein said HMG-CoA reductase inhibitor is a statin.

9. The method of claim 8, wherein said at least one statin comprises compactin, lovastatin, simvastatin, pravastatin, mevastatin, fluvastatin, rosuvastatin, atorvastatin, pitavastatin, cervistatin, berivastatin, dalvastatin, glenvastatin, or a combination thereof.

10. The method of claim 8, wherein said at least one statin has an RI value of 0.2 to 0.7 and said composition is administered topically to at least one eye of said patient.

11. The method of claim 8, wherein said HMG-CoA reductase inhibitor has the formula A-B, wherein:

A = 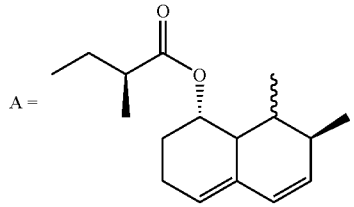

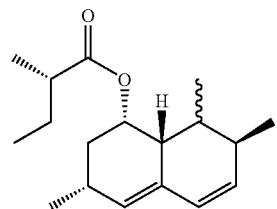

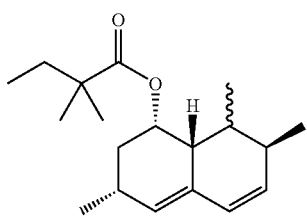

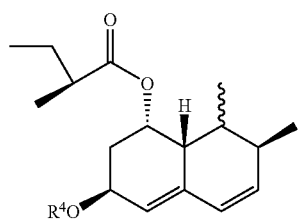

-continued

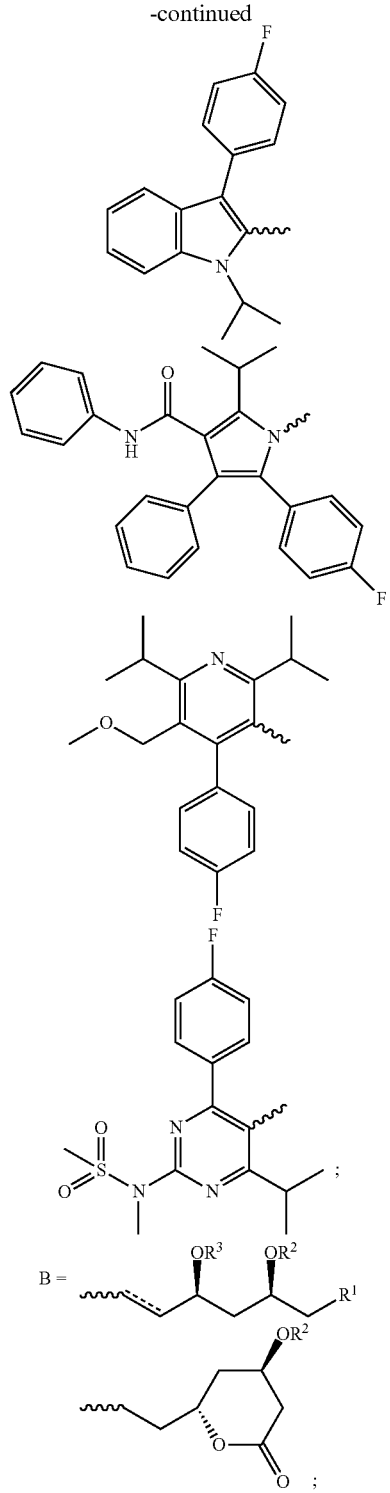

$R^1$=$CO_2R$, $CONR^5R^6$ or $CH_2OR^7$, or $R^1$ and $R^3$ form a lactone;

R=H or a cationic salt moiety, or $CO_2R$ forms a pharmaceutically acceptable ester moiety;

$R^2$, $R^3$, $R^4$=same or different=H, $C(O)R^8$ or $C(O)NR^5R^6$;

$R^5$, $R^6$=same or different=H or alkyl;

$R^7$=H or $C(O)R^8$; and $R^8$=alkyl.

12. The method of claim 8, wherein said HMG-CoA reductase inhibitor is a HMG-CoA reductase inhibitor including one of the structures of B:

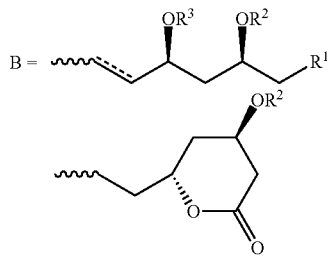

wherein:
R$^1$=CO$_2$R, CONR$^5$R$^6$ or CH$_2$OR$^7$, or R$^1$ and R$^3$ together form a lactone;
R=H or a cationic salt moiety, or CO$_2$R forms a pharmaceutically acceptable ester moiety;
R$^2$, R$^3$, same or different H, C(O)R$^8$ or C(O)NR$^5$R$^6$;
R$^5$, R$^6$=same or different=H or alkyl;
R$^7$=H or C(O)R$^8$; and
R$^8$=alkyl.

13. The method of claim 8, wherein said composition is administered topically to at least one eye of said patient.

14. The method of claim 8, wherein said HMG-CoA reductase inhibitor comprises from about 0.05% to about 2.0% by weight of said composition.

15. A method of controlling normal or elevated intraocular pressure in a patient which comprises administering a pharmaceutically effective amount of a composition comprising at least one HMG-CoA reductase inhibitor to said patient, wherein said HMG-CoA reductase inhibitor is at least one statin.

16. The method of claim 15, wherein said at least one statin comprises compactin, lovastatin, simvastatin, pravastatin, mevastatin, fluvastatin, rosuvastatin, atorvastatin, pitavastatin, cervistatin, berivastatin, dalvastatin, glenvastatin, or analog thereof, or a combination thereof.

17. The method of claim 15, wherein said at least one statin has an RI value of 0.2 to 0.7 and said composition is administered topically to at least one eye of said patient.

18. The method of claim 15, wherein said HMG-CoA reductase inhibitor is:

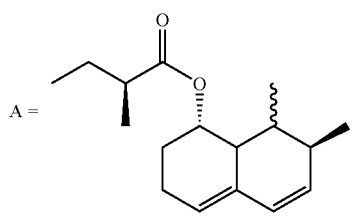

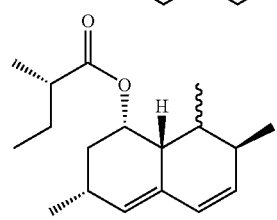

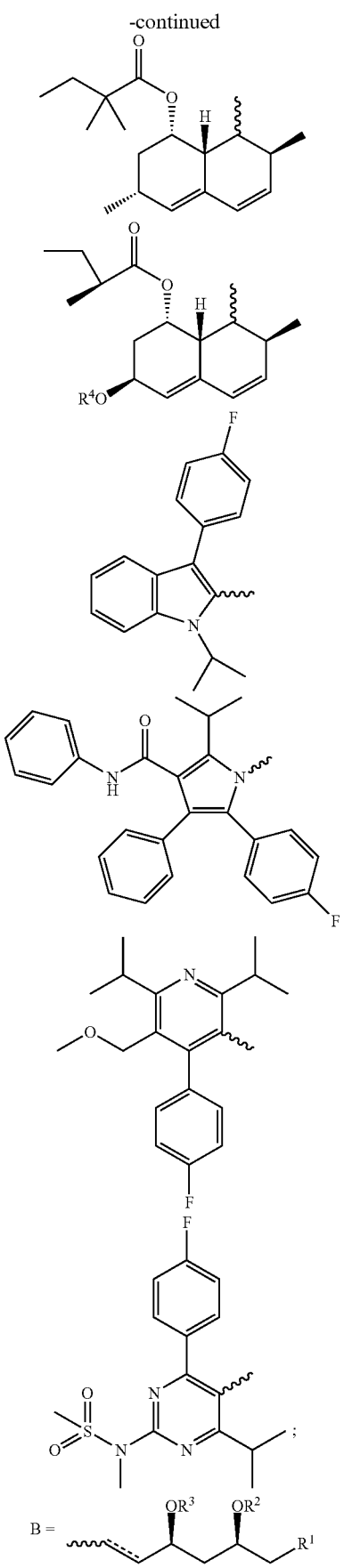

-continued

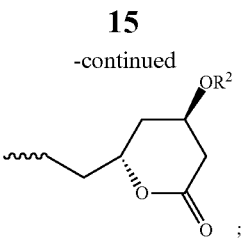

R¹=CO₂R, CONR⁵R⁶ or CH₂OR, or R¹ and R³ form a lactone;
R=H or a cationic salt moiety, or CO₂R forms a pharmaceutically acceptable ester moiety;
R², R³, R⁴=same or different=H, C(O)R⁸ or C(O)NR⁵R⁶;
R⁵, R⁶=same or different=H or alkyl;
R⁷=H or C(O)R⁸; and
R⁸=alkyl.

19. The method of claim 15, wherein said composition is administered topically to at least one eye of said patient.

20. The method of claim 15, wherein said HMG-CoA reductase inhibitor comprises from about 0.05% to about 2% by weight of said composition.

* * * * *

UNITED STATES PATENT AND TRADEMARK OFFICE
CERTIFICATE OF CORRECTION

PATENT NO. : 8,415,364 B2
APPLICATION NO. : 10/580477
DATED : April 9, 2013
INVENTOR(S) : David L. Epstein et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 828 days.

Signed and Sealed this
Twenty-ninth Day of October, 2013

Teresa Stanek Rea
*Deputy Director of the United States Patent and Trademark Office*

UNITED STATES PATENT AND TRADEMARK OFFICE
CERTIFICATE OF CORRECTION

PATENT NO.       : 8,415,364 B2                                                                 Page 1 of 1
APPLICATION NO. : 10/580477
DATED            : April 9, 2013
INVENTOR(S)      : Epstein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1452 days.

Signed and Sealed this
First Day of September, 2015

Michelle K. Lee
*Director of the United States Patent and Trademark Office*